United States Patent
Bonrath et al.

(10) Patent No.: US 6,455,707 B1
(45) Date of Patent: Sep. 24, 2002

(54) PROCESS FOR THE PREPARATION OF SUBSTITUED PYRANES

(75) Inventors: Werner Bonrath, Freiburg (DE); Fabio Cirillo, Winterthur (CH)

(73) Assignee: Roche Vitamins, Inc., Parsippany, NJ (US)

( * ) Notice: Subject to any disclaimer, the term of this patent is extended or adjusted under 35 U.S.C. 154(b) by 0 days.

(21) Appl. No.: 09/943,669

(22) Filed: Aug. 31, 2001

(51) Int. Cl.[7] ............................................. C07D 309/04
(52) U.S. Cl. ....................................... 549/356
(58) Field of Search ........................... 549/356; 502/60; 204/157.15; 427/487

(56) References Cited

FOREIGN PATENT DOCUMENTS

| BE | 852918 | 7/1977 |
| EP | 0 949 254 A1 | 10/1999 |

OTHER PUBLICATIONS

Serra, "Bisabolane Sesquiterpenes: Synthesis of (R)–(+)–Sydowic Acid and (R)–(+)–Curcumene Ether," *Synlet*, vol. 6, pp. 890–892 (2000).

Erman, et al., "The Rearrangement of Tertiary Propargl Alcohols to d,β–Unsaturated Aldehydes in the Presence of Polymeric Organosilyl Vanadates," *Tetrahedron Letters*, No. 34, pp. 2981–2984 (1976).

English abstract of Belgian Patent No. 852 918 (1977).

Abstract of Strickler, et al., "Essential Oils. V. Two Monoterpene Oxides From So–Called Distilled Lime Oil," *Helv. Chem. Acta.*, 49(7), pp. 2055–2067 (1966).

Primary Examiner—Joseph K. McKane
Assistant Examiner—Jennifer C. Murphy
(74) Attorney, Agent, or Firm—Bryan Cave, LLP

(57) ABSTRACT

Substituted pyranes such as 2-ethinyl-tetrahydro-2,6,6-trimethylpyran are prepared from dehydrolinalool or higher homologues thereof by heating or treatment with microwaves in the presence of a solid acid.

7 Claims, No Drawings

PROCESS FOR THE PREPARATION OF SUBSTITUED PYRANES

FIELD OF THE INVENTION

The present invention relates to a novel process for the preparation of substituted pyranes of the general formula I

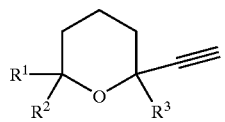

(I)

wherein $R^1$, $R^2$ and $R^3$ are lower alkyl.

BACKGROUND OF THE INVENTION

The compounds of formula I belong to a known class of compounds. For instance, the compound of formula I wherein each of $R^1$, $R^2$ and $R^3$ is methyl, 2-ethinyl-tetrahydro-2,6,6-trimethylpyran, is a known intermediate, e.g., in the manufacture of flavours and has been prepared so far from dehydrolinalool by ring closure catalyzed by tungsten, molybdenum or polyphosphoric acid (Strickler et al., Helv. Chem. Acta 1966, 49, 2055; Erman et al., Tetrahedron 1976, 34, 2981 and Belgian Patent No. 852 918).

SUMMARY OF THE INVENTION

In accordance with the present invention it has been found that the compounds of formula I can be conveniently prepared by exposing a compound of the general formula II

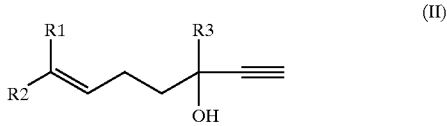

(II)

wherein $R^1$, $R^2$ and $R^3$ are as above, in the presence of a solid acid to elevated temperature or irradiation with microwaves.

DETAILED DESCRIPTION OF THE INVENTION

The process of the present invention proceeds in high yields and in short reaction time. Further, the process of the present invention has the advantage that the use of a solvent and unwanted pressure increase in closed reaction vessels is avoided.

The term "microwave" as used herein refers to the region of the electromagnetic spectrum having frequencies of 30 GHz to 300 MHz thus corresponding to wavelengths of 1 cm to 1 m. In order not to interfere with wavelengths for Radar (1 cm–25 cm), household or industrial microwave heaters are required to operate at either 12.2 cm (2.45 GHz) or 33.3 cm (918 MHz). Thus, in a preferred embodiment of the invention, the term microwaves refers particularly to such wavelenghts. In the process of this invention, conventional microwave equipment can be used. Microwave equipment suitable in the process of this invention is supplied, e.g., by the firms MLS, Leutkirch, Germany (Lavis Multiquant 1000); or MILESTONE Inc., Monroe, Conn. 06468, USA (Ethos reactors). Conveniently, the irradiation in the process of this invention is carried out applying a power of irradiation of from about 600 W to 1200 W, more preferably from about 800 W to about 1000 W.

As used herein, "solid acid" means an ordered solid having defined acidic centers selected from Lewis and Bronstedt centers Such centers may be engineered to control which reaction product is favored in a particular reaction. Thus, solid acids, which may be used as catalysts in the present invention not only accelerate the rate of the reaction, but in reaction systems where multiple products may be formed, they may strongly influence which of the products is produced in the greatest amount. The solid acid used as a catalyst in the present invention is suitably a strong organic acid, such as a polymeric sulfonic acid, e.g., a polyperfluoroalkylene sulfonic acid, particularly Deloxan® ASP (Degussa, Frankfurt/M., Germany) or Nafion® NR 50 (DuPont, Wilmington, Del.,USA), or an anionic ion exchange resin such as Amberlyst® 15 (Rohm & Haas, Philadelphia, Pa.,USA); or an inorganic acid, such as sulfuric acid/silizium dioxide, or silicates such as zeolithes, e.g., Zeocat®, and Wessalith® types (Degussa), montmorillonites, e.g. Montmorillonit K 10 and KSF (Fluka, Buchs, Switzerland) and mesoporous (pore size 2–50 nm) metal-doped silica gels (Degussa).

Particularly preferred are microporous (pore size<2 nm) zeolithes such as Wessalith®Day P and and Zeocat® types such as Zeocat Z6–05–02.

In a preferred aspect, $R^1$, $R^2$ and $R^3$ are each methyl. However, any compound of the general formula I wherein $R^1$, $R^2$ and $R^3$ are, independently, lower alkyl, can be prepared by the process of this invention. The term lower alkyl as used herein denotes straight or branched chain alkyl groups having up to 7 carbon atoms, such as methyl, ethyl, propyl, isopropyl, n-butyl, sek.butyl, tert.butyl, n-pentyl and isomers thereof.

If the process of the presence invention is carried out by exposing the compound of formula II to elevated temperature, the compound of formula II is heated, in the presence of a solid acid, to a temperature of about 40° C. to about 100° C., preferably of about 60° C. to about 100° C. However, in a preferred aspect, the present invention relates to the preparation of a compound of formula I wherein a compound of the general formula I is excposed to microwave irradiation.

The process according to the present invention is carried out in dry state, i.e., in the absence of solvents. Prior to exposure to elevated temperature or irradiation, the starting compound of formula II is suitably thoroughly mixed with the catalyst, e.g., by suspending the catalyst in a solution of the compound of formula II, e.g., in dichloromethane or an ether such as methyl-tert.butyl ether, with stirring and subsequent removal of the solvent or, if the catalyst is a porous material, simply adding the compound of formula II to the catalyst. The catalyst is suitably used in an amount of about 0.5 to about 10, preferably about 1 to about 2 parts of weight per part of weight of compound of formula II.

The following Examples illustrate the invention further. The reactions were carried out under Ar atmosphere. The microwave equipment used was Lavis Multiquant 1000 (MLS). ETTP means 2-ethynyl-tetrahydro-2,6,6-trimethylpyran; DLL means D,L-3,7-dimethyl-6-octen-1-in-3-ol (dehydrolinalool).

EXAMPLES

Example 1

A solution of 13.82 g (0.09 mol) of dehydrolinalool (II, $R^1$, $R^2$ and $R^3$ =methyl) in 200 ml of methyl tert.butyl ether was added to 28.35 g of Zeocat® Z6–05–02 and stirred for 30 min. The reaction mixture was evaporated (40° C., 300 mbar) and the resulting solid was subjected to microwave irradiation (600 W power for 4 s). The product was separated from the solid by dissolving in 300 ml acetone and evaporating the solvent in vacuo. The crude 2-ethinyl-tetrahydro-2,6,6-trimethylpyran was obtained in 13.30 g (96.2%) yield as yellowish liquid.

Example 2

In analogy to the procedure of Example 1 but substituting other solid acid catalysts for Zeocat® Z6–05–02 the following results were obtained:

| catalyst | reaction time [sec] | yield ETTP [%] | amount DLL [%] | conversion [%] |
|---|---|---|---|---|
| a) Deloxan ® ASP | 10 | 84.0 | 14.9 | 85.1 |
| b) Amberlys ® 15 | 10 | 80.0 | 19.5 | 80.5 |
| c) Fulmont ® XMP3 | 36 | 63.1 | 36.1 | 63.9 |
| d) Montmorillonit K10 | 15 | 76.4 | 20.9 | 79.1 |
| e) Montmorillonit KSF | 20 | 62.3 | 37.1 | 62.9 |
| f) Nafion ® NR 50 | 63 | 32.6 | 67.4 | 32.6 |
| g) H2SO4/SiO2 | 4 | 96.6 | 3.4 | 96.6 |
| h) Wessalith ® Day P | 4 | 99.1 | 0.0 | 100 |
| i) mesoporeous silica gel | 60 | 8.0 | 85.0 | 15.0 |
| j) mesoporeous silica gelH+ – form | 0 | 43.0 | 55.0 | 45.0 |

Example 3

The procedure of Examples 1 and 2 was repeated re-using the catalysts recovered from the first run in two further runs. The results were as shown below:

| Catalyst | run 1 | run 2 | run 3 | run 1 | run 2 | run 2 |
|---|---|---|---|---|---|---|
| Deloxan ® ASP | 84.1 | 83.9 | 82.9 | 85.1 | 84.2 | 94.3 |
| Wessalith ® DayP | 99.1 | 97.8 | 97.5 | 99.1 | 97.9 | 96.3 |
| Zeocat ® Z6-05-02 | 96.2 | 98.3 | 96.9 | 96.4 | 98.5 | 99.0 |

Example 4

D,L-3,7-dimethyl-6-octen-1-in-3-ol (DDL) (0.92 g, 6 mmol) was adsorbed on the solid acid (2 g). After evaporation of the solvent (experiments using mesoporeous silica gel were carried out with a solution of DDL in methyl tert.butyl ether (MTBE); experiments using Wessalith® Day P were carried out without solvent), the solid was stirred for 60 min at room temperature, 40° C., 60° C., 80° C., and 100° C. After cooling to room temperature, the organic material was desorbed with 250 ml MTBE, and the organic layer was concentrated in vacuum (40° C., 50 mbar). The crude product was analyzed by GC. The results are summarized below:

| Catalyst | reaction temperature [° C.] | yield ETTP [%] |
|---|---|---|
| Wessalith | room temperature | 8 |
| Wessalith | 40 | 29 |
| Wessalith | 60 | 77 |
| Wessalith | 80 | 71 |
| Wessalith | 100 | 69 |
| mesoporeous silica gel-H+ | room temperature | 10 |
| mesoporeous silica gel-H+ | 40 | 26 |
| mesoporeous silica gel-H+ | 60 | 89 |
| mesoporeous silica gel-H+ | 80 | 96 |
| mesoporeous silica gel-H+ | 100 | 92 |

Example 5

500 ml (456.6 g, 2.87 mol) of DLL and 16 g of Amberlyst 15 were heated to 70° C. After 7 h reaction time the conversion was 92% (control by gaschromatography). The mixture was distillated at 99.4° C./147 mbar. There were thus obtained 370 g of ETTP (purity 97.32%), corresponding to a yield of 82.4%.

The invention being thus described, it will be obvious that the same may be varied in many ways. Such variations are not to be regarded as a departure from the spirit and scope of the invention and all such modifications are intended to be included within the scope of the following claims.

What is claimed is:

1. Process for the preparation of compounds of the general formula I

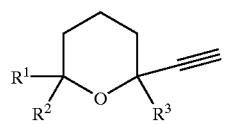

(I)

wherein $R^1$, $R^2$ and $R^3$ are lower alkyl, which comprises exposing a compound of the general formula II

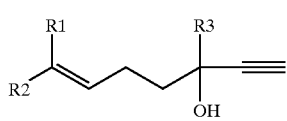

(II)

wherein $R^1$, $R^2$ and $R^3$ are as above, in the presence of a solid acid to elevated temperature or irradiation with microwaves.

2. A process as in claim 1, wherein a compound of formula II is irradiated with microwaves in the presence of a solid acid.

3. A process as in claim 1 or 2, wherein the solid acid is a zeolithe.

4. A process as in claim 1, wherein the amount of solid acid used is about 0.5 to about 10 parts by weight per part by weight of a compound of formula II.

5. A process as in claim 1, wherein a microwave source of about 800 to about 1000 W is used.

6. A process as in claim 1, wherein in the compound of formula II $R^1$, $R^2$ and $R^3$ are methyl.

7. A process according to claim 4, wherein the amount of solid acid used is about 1 to about 2 parts by weight per part by weight of a compound of formula II.

\* \* \* \* \*

UNITED STATES PATENT AND TRADEMARK OFFICE
CERTIFICATE OF CORRECTION

PATENT NO. : 6,455,707 B1 Page 1 of 1
DATED : September 24, 2002
INVENTOR(S) : Werner Bonrath and Fabio Cirillo It is certified that error appears in the above-identified patent and that said Letters Patent is hereby corrected as shown below:

<u>Title page,</u>
Item [54], please change "SUBSTITUED" to -- SUBSTITUTED --;
Item [30], Priority Data is missing. Therefore, please insert:

-- [30] Foreign Application Priority Data
September 6, 2000 (EP) .................. 00119257.4 --;
Item [56], OTHER PUBLICATIONS, in the first line of the "Erman reference, please change "Propargl" to -- Propargyl --.

Signed and Sealed this

Eighth Day of April, 2003

JAMES E. ROGAN
*Director of the United States Patent and Trademark Office*